(12) United States Patent
    Plotkin

(10) Patent No.: US 9,757,175 B2
(45) Date of Patent: Sep. 12, 2017

(54) UNIVERSAL BONE SCREW SCREWDRIVER

(71) Applicant: David B. Plotkin, Springfield, NJ (US)

(72) Inventor: David B. Plotkin, Springfield, NJ (US)

( * ) Notice: Subject to any disclaimer, the term of this patent is extended or adjusted under 35 U.S.C. 154(b) by 0 days.

(21) Appl. No.: 14/827,929

(22) Filed: Aug. 17, 2015

(65) Prior Publication Data

US 2016/0038210 A1    Feb. 11, 2016

Related U.S. Application Data

(63) Continuation-in-part of application No. 13/295,738, filed on Nov. 14, 2011, now Pat. No. 9,107,721.

(60) Provisional application No. 61/456,746, filed on Nov. 12, 2010.

(51) Int. Cl.

| A61B 17/88 | (2006.01) |
|---|---|
| B25B 23/14 | (2006.01) |
| B25B 23/00 | (2006.01) |
| B25B 15/00 | (2006.01) |
| A61B 17/00 | (2006.01) |
| A61B 19/00 | (2006.01) |

(52) U.S. Cl.
    CPC ........ *A61B 17/8875* (2013.01); *B25B 15/005* (2013.01); *B25B 23/0035* (2013.01); *B25B 23/141* (2013.01); *A61B 2017/00464* (2013.01); *A61B 2019/301* (2013.01)

(58) Field of Classification Search
    CPC .. B25B 23/142; B25B 23/141; B25B 23/1422
    See application file for complete search history.

(56) References Cited

U.S. PATENT DOCUMENTS

| 6,308,598 B1 | 10/2001 | O'Neil | |
| 7,347,129 B1 * | 3/2008 | Youtsey | ................. B25B 13/06 |
| | | | 81/124.2 |
| 2006/0236822 A1 | 10/2006 | Nish | |
| 2009/0266204 A1 | 10/2009 | Rinner | |

* cited by examiner

*Primary Examiner* — David Bates
(74) *Attorney, Agent, or Firm* — Stroock & Stroock & Lavan LLP

(57) ABSTRACT

The instant invention is directed to a universal bone screw screwdriver and in particular to a universal screwdriver that permits the removal of screws from bone plates that are manufactured by different manufacturers having distinct characteristics. The universal bone screw screwdriver comprises a handle that is adapted to removeably receive an elongated tool bit having a hollow center. The elongated tool bits correspond to the screw heads of different manufacturers. The universal bone screwdriver further comprises a torque limiting and locking spring to secure the elongated tool bit to the handle and inhibit over-tightening of the bone screw into the bone or bone plate as the case may be.

4 Claims, 10 Drawing Sheets

UNIVERSAL BONE SCREW SCREWDRIVER

CROSS REFERENCE TO RELATED APPLICATIONS

This application is a continuation in part of U.S. patent application Ser. No. 13/295,738 filed Nov. 12, 2011 and also claims priority to U.S. Provisional Patent Application No. 61/456,746 filed Nov. 12, 2010, entitled UNIVERSAL BONE SCREW SCREWDRIVER, the entire disclosure of which is incorporated herein by reference.

BACKGROUND OF THE INVENTION

Field of the Invention

The embodiments of the present invention relate to a universal bone screw screwdriver for use with interchangeable tool bits made by different screw and bone plate manufacturers. More specifically, the invention relates to a universal bone screw screwdriver that allows for a user to select the tool bit that is compatible with the screw that the user is trying to manipulate and further can prevent the user from over-tightening the screw in the bone or the bone plate.

Description of Related Art

Heretofore, use of bone screws and bone plates have become a significant aide in the treatment of bone fracture repair. There are numerous manufacturers that supply the plates and bone screws to hospitals and other surgical centers to permit open reduction internal fixation. Although the efficacy of the bone plates and bone screws has been established as a standard of care over many years, certain problems have arisen regarding the after care that may occur with respect thereto. For example, when a patient that has an open reduction internal fixation procedure performed and is suddenly brought to an emergency room for treatment, it is incumbent upon the hospital or treatment facility to have an inventory of each of the screwdrivers necessary to remove each company's particular screws. Because each company uses different types of screws, it is not assured that the hospital or treatment facility will have the correct screwdriver. Further, even if the appropriate screwdriver is available, it is not assured that that there will be time to sterilize the screwdriver for several hours as is required by emergency room protocol.

Accordingly, a universal screwdriver that is suitable for use with the screw heads of each manufacturer of screw and bone plates is desirable.

SUMMARY OF THE INVENTION

Generally speaking, in accordance with the invention, a universal screwdriver capable of removing screws made by different bone screw and plate manufacturers is provided. A driver shaft is adapted to receive interchangeable tool bits that are suitable for use with the screw heads of different manufacturers. A recess is disposed in the driver shaft for receiving a torque limiting spring which will secure the tool bit in the shaft. The torque limiting spring is removable and hence, permits the tool bit to be replaceably removed from the shaft and further, when the tool bit is disposed in the driver shaft the torque limiting spring inhibits over tightening of the bone screws.

A second embodiment of the present invention comprises an elongated tool bit that is suitable to for use with the screw heads of different manufacturers. A recess is disposed along the handle for receiving a torque-limiting spring which will secure the elongated tool bit to the handle. The torque limiting spring is removable and hence, permits the elongated tool bit to be replaceably removed from the handle and further, when in use, the torque limiting spring inhibits over tightening of the bone screws. The elongated tool bit may be hollow to allow the screwdriver to be used in conjunction with Kershner wires and cannulated screws.

Accordingly, an object of the instant invention is to provide an improved universal screwdriver for use with the bone screws of many companies.

BRIEF DESCRIPTION OF THE DRAWINGS

In the drawing figures, which are merely illustrative, and wherein like reference characters denote similar elements throughout the several views.

DETAILED DESCRIPTION OF EXEMPLARY EMBODIMENT

Figure 1:
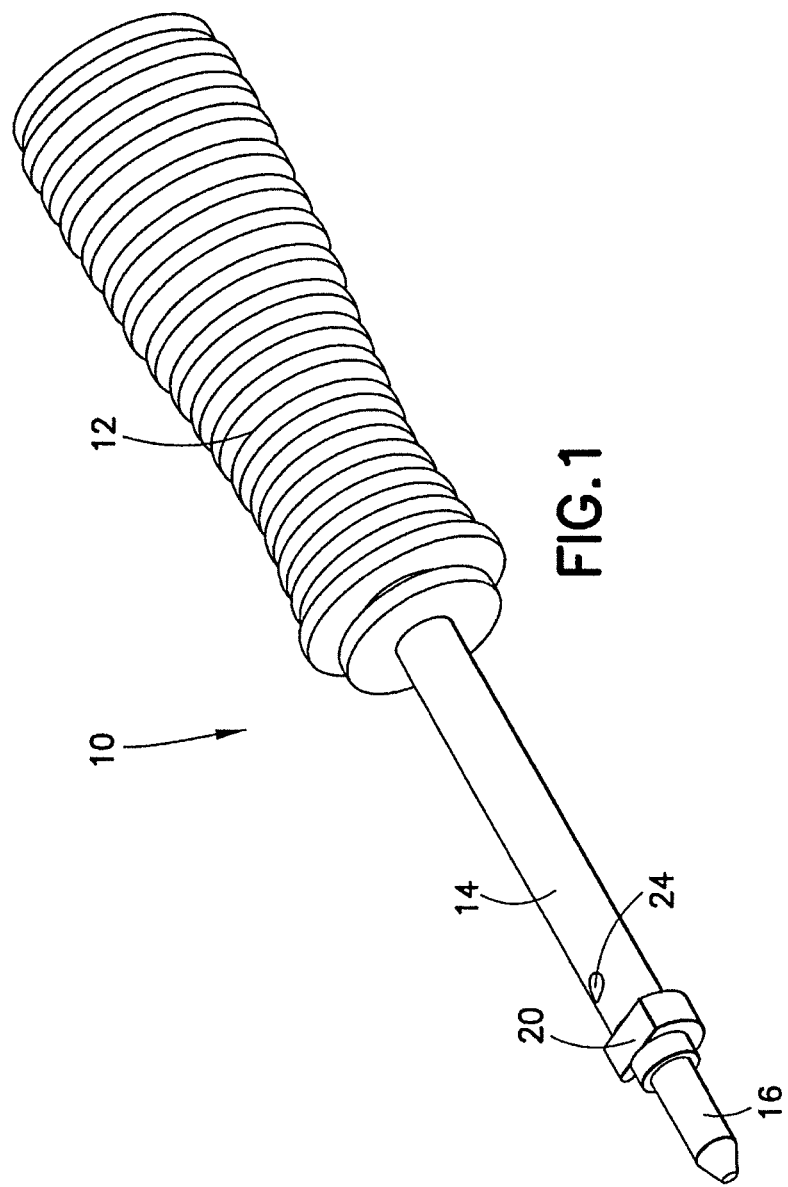
FIG. 1 is a perspective view of the universal screwdriver constructed with a preferred embodiment of an embodiment of the instant invention.

Generally speaking, in accordance with the instant invention, a universal screwdriver generally indicated as 10 in FIG. 1 is provided. In the embodiment depicted in FIGS. 1, 2 and 3, the universal screwdriver includes a handle 12, a driver shaft 14, a tool bit 16, a recess 30 and a torque limiting spring 20. With specific references to FIGS. 2, 3 and 4, the tool bit illustrated therein is representative of the type of screws manufactured by numerous different companies, such as Synthes, Ostiomed, Villex, and Stryker as well as other orthopedic device manufacturers.

Figure 2:
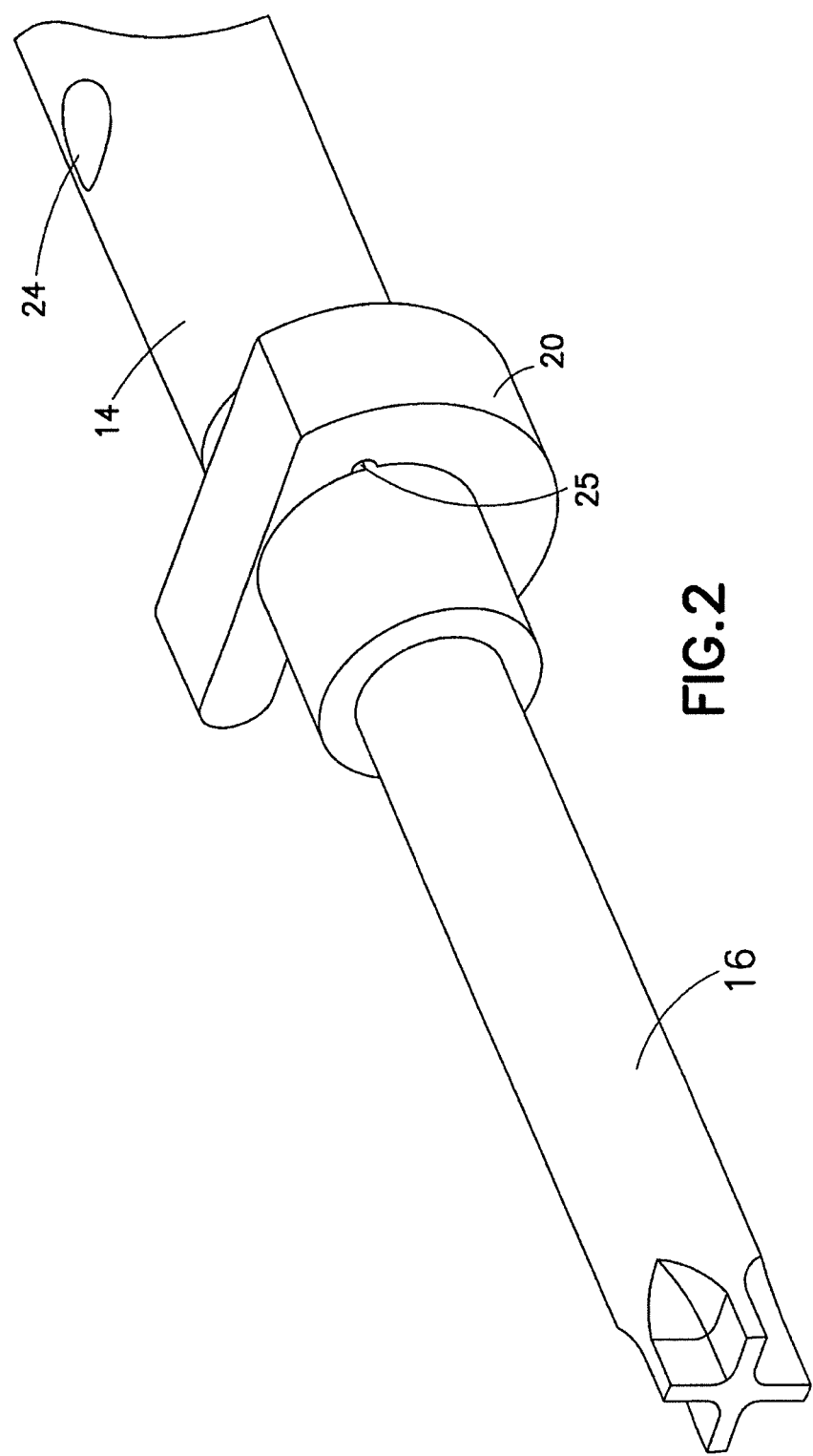
FIG. 2 is a perspective view of the driver shaft and tool bit interface constructed in accordance with an embodiment of the instant invention.

As illustrated in FIG. 2, the tool bit design will have a unique configuration such as a cruciform or hexagram or other types of configurations and each manufacturer has a tool bit configuration that is unique to the company. These tool bit configurations are designed to mate with a screw and hence, the screwdrivers provided by each company are not suitable for use with the screws of another company.

Figure 3:
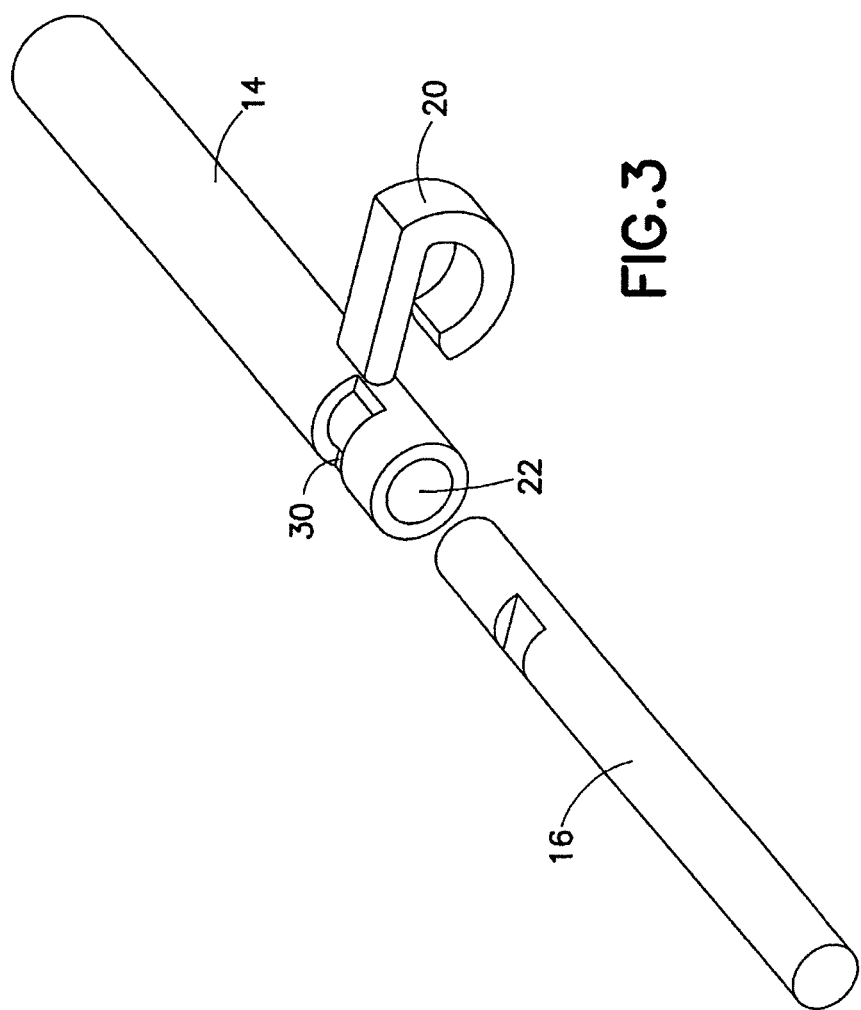
FIG. 3 is an exploded view of the driver shaft, tool bit and torque limiting spring constructed in accordance with an embodiment of the instant invention.
Figure 4:
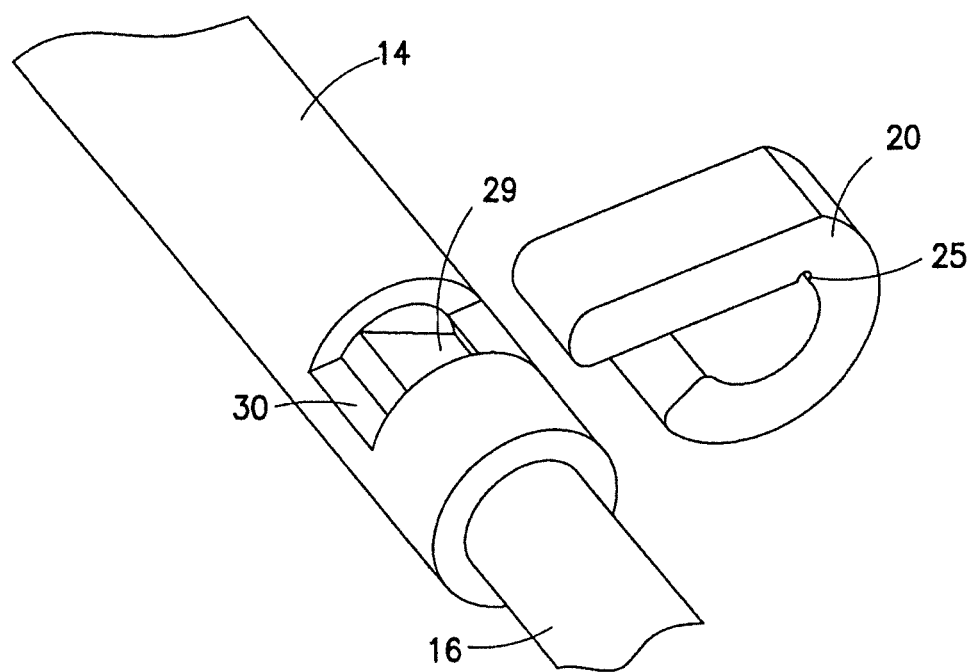
FIG. 4 is an exploded view of the tool bit visible through the recess.

Accordingly, tool bit 16 illustrated in FIGS. 2, 3 and 4, is by way of example only, and is not limiting in any sense to the instant invention.

The driver shaft 14 is connected to the handle 12 as depicted in FIG. 1. One of ordinary skill in the art would appreciate the mechanism by which the driver shaft 14 is connected to the handle.

Figure 5:
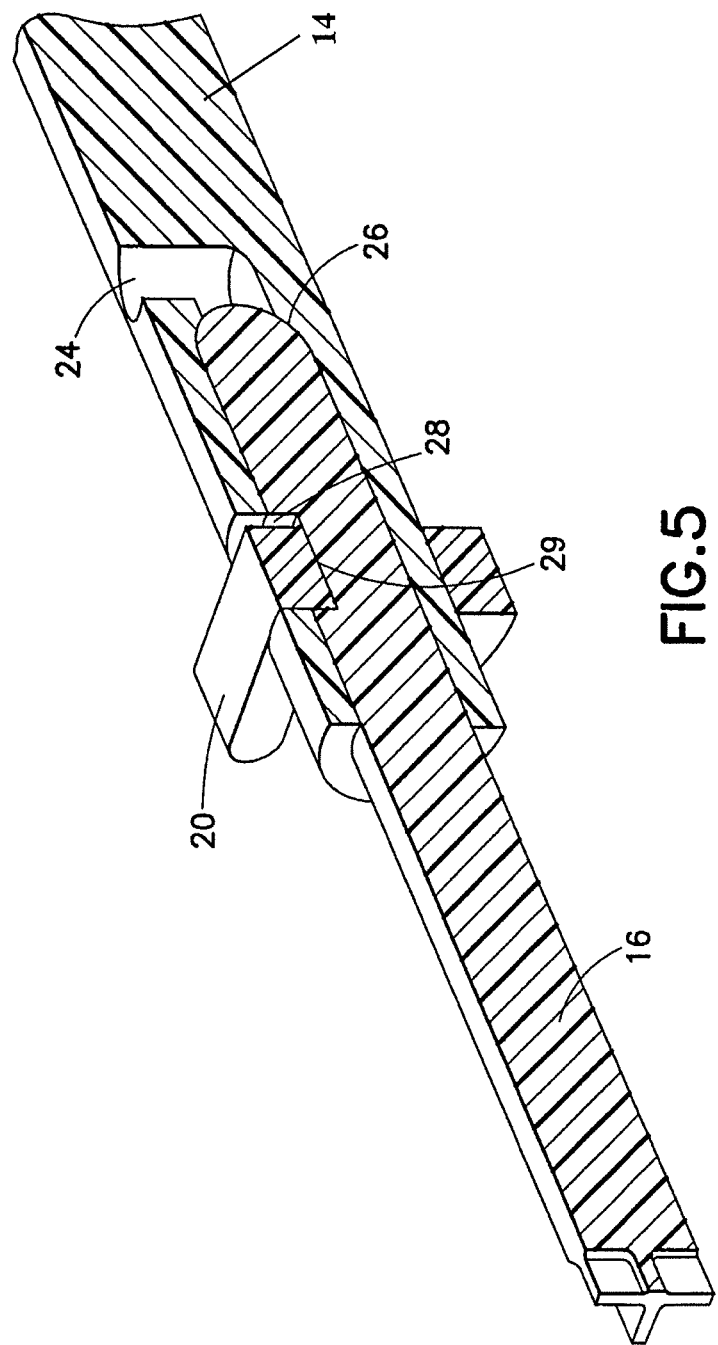
FIG. 5 is a sectional view of the driver shaft securing a tool bit using the torque limiting spring in accordance with an embodiment of the instant invention.

As illustrated in FIG. 3, a recess 30 is disposed on the driver shaft 14 which can allow the inside of the driver shaft 14 to be externally visible. An elongated opening 22 extends through the driver shaft 14. The shank of the tool bit 16 has a uniformed cross-sectional dimension and is adapted to be received in the opening 22. The shank of the tool bit is inserted into the opening 22 formed in driver shaft 14 and comes to rest at the thrust bearing surface 26 inside the driver shaft 14 as shown in FIG. 5. A slot 28, which includes a flat 29 (as shown in FIG. 4), is provided in each of the tool bits and is brought into alignment with the recess 30 formed in the each shaft on the tool bit. When the shaft of the tool bit is inserted up, into and against the thrust bearing surface 26 so that the tool bit is brought into alignment with the recess 30 in the driver shaft 14, a locking mechanism can be inserted to secure the tool bit within the driver shaft 14.

In one embodiment, the torque limiting spring 20 is the locking mechanism to secure the tool bit into the driver shaft 14 as depicted in FIGS. 3 and 4. One of ordinary skill in the art would appreciate other methods by which the tool bit can be locked into the driver shaft 14.

Figure 7:
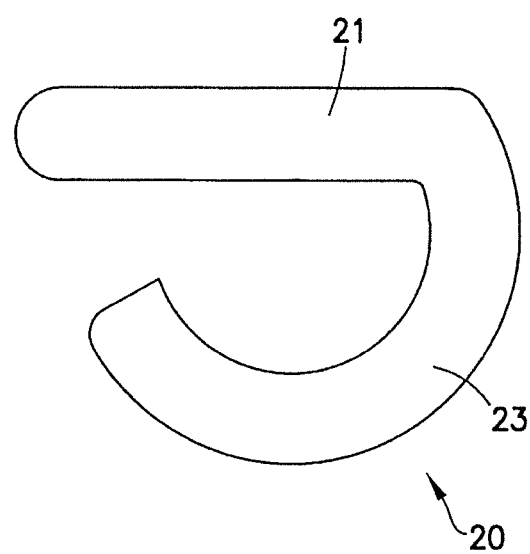
FIG. 7 is an elevational view of a torque limiting spring to be used in accordance with an embodiment of the instant invention.

The preferred dimensions of the torque limiting spring are depicted in FIG. 7, but by no means is limiting in any sense to the instant invention. When the slot 28 of the tool bit is brought into alignment with the recess 30, the torque limiting spring 20 is inserted in the recess 30 to secure the tool bit 16 into the driver shaft 14 and thereby preventing any actual displacement of the tool bit. Removal of the spring to permit replacement of the tool bit is provided by snapping the torque limiting spring 20 on or off thereby permitting the tool bit to be easily removed or attached.

Additionally, in this position, the torque limiting spring 20 will rest against the flat 29 during each rotation of the handle 12 and will inhibit the over-tightening of the screw in the bone or in the plate as the case may be. When the tool bit 16 is engaged with the screw, as the user rotates the handle 12, the tool bit 16 will encounter resistance from turning the screw into the bone or bone plate. As torque is applied to the bone screw, the torque limiting spring 20 will start to be lifted by the flat 29. When the torque applied to the bone screw reaches the pre-set torque value of the torque limiting spring 20, the torque limiting spring 20 will become disengaged from the flat 29. At this point, the driver shaft 14 can continue to be rotated, but the tool bit 16 will have ceased rotating, thus inhibiting a user from over-tightening a screw into the bone or bone plate. The user can select the desired torque limitation by utilizing a torque limiting spring 20 that conforms to the user's needs.

Figure 6:
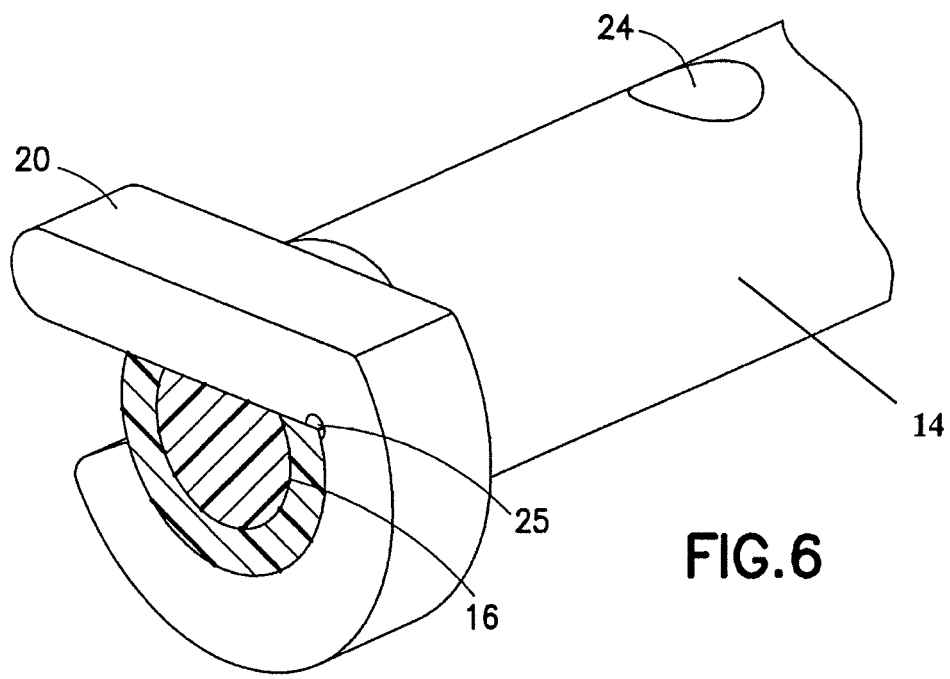
FIG. 6 is a sectional view showing the manner in which the torque limiting spring is connected to the driver shaft and is used to inhibit over-tightening of the screw in accordance with an embodiment of the instant invention.

In one embodiment, the torque limiting spring 20 comprises a flat arm 21 flexibly connected on one end to a semicircular arm 23 as depicted in FIG. 7. In another embodiment, the torque limiting spring 20 further comprises a notch 25 on the interior surface where the flat arm 23 is flexibly connected to the semicircular arm 25 as depicted in FIGS. 2, 4, and 6.

In another embodiment, a flush hole 24 may be disposed on the driver shaft 14. The flush hole 24 extends into the thrust bearing surface 26. When a flush hole 24 is provided, the thrust bearing surface 26 does not extend through the entire diameter of the driver shaft 14. Rather the thrust bearing surface 26 extends perpendicularly to the wall of the driver shaft 14 such that the area behind the tool bit 16 is accessible. In this manner, the flush hole 24 permits the area that receives the shaft of the tool bit 16 to be easily autoclaved and cleaned and any bone debris can be removed between usages.

Figure 10:
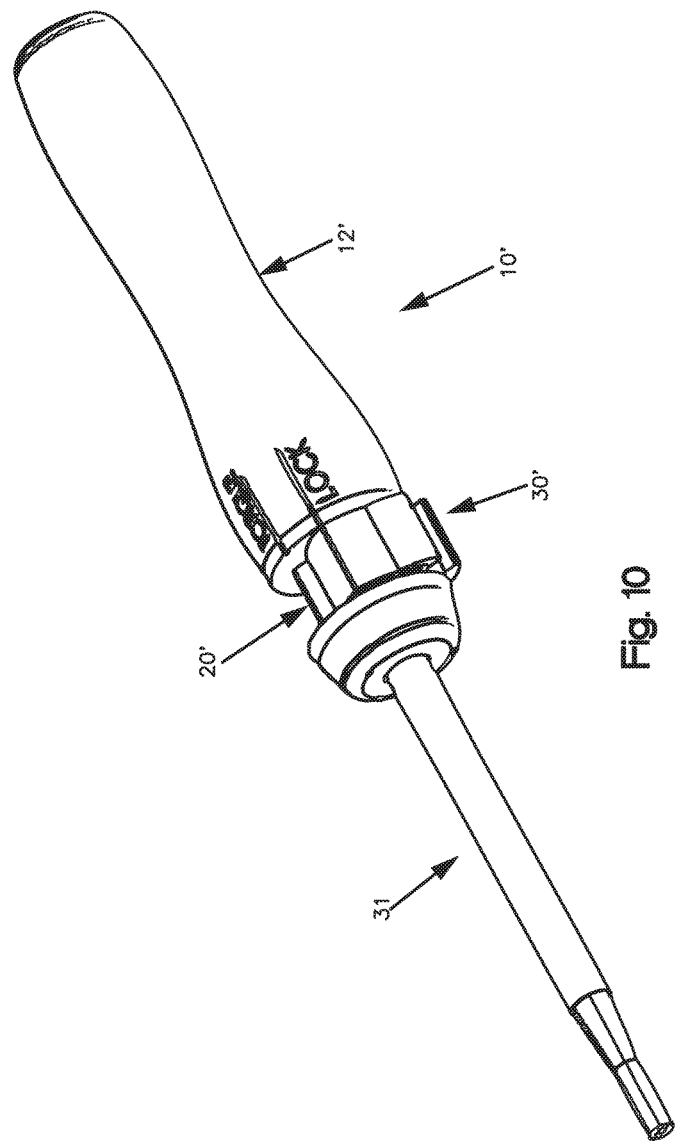
FIG. 10 is a perspective view of the universal screwdriver constructed as an embodiment of the instant invention.
Figure 11:
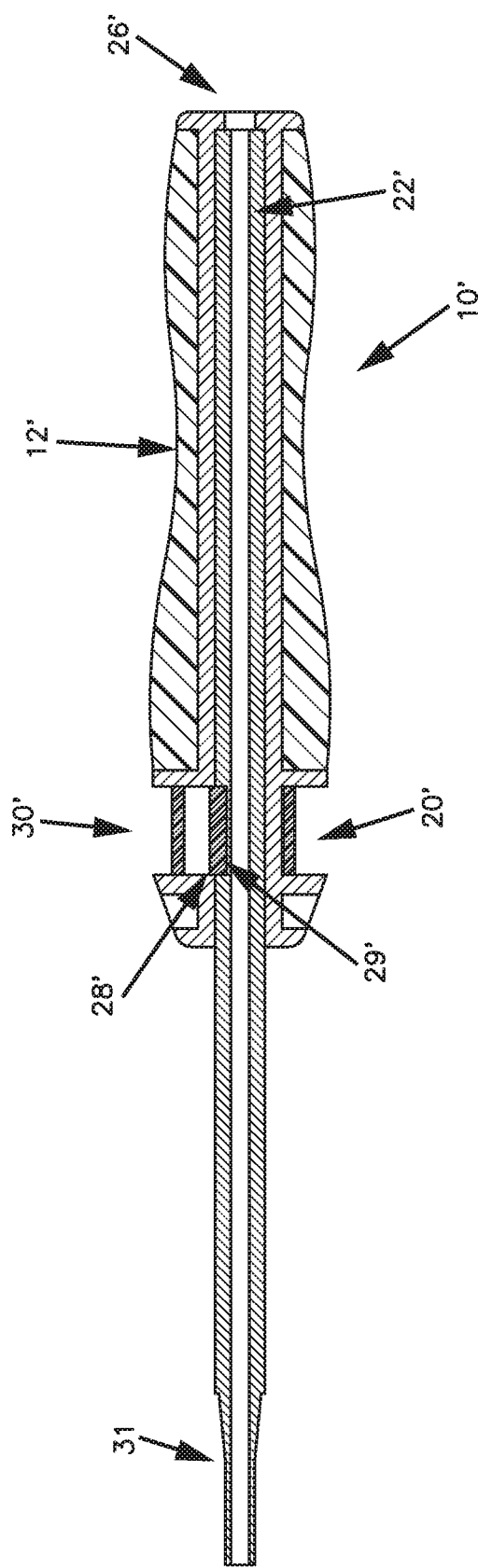
FIG. 11 is a cross-sectional view of universal screwdriver constructed as an embodiment of the instant invention.

In another embodiment, with like numerals used to reference like elements in the embodiments described above, a universal screwdriver generally indicated as 10' in FIGS. 10-11 is provided. In the embodiment depicted in FIGS. 10-11, the universal screwdriver includes a handle 12', an elongated tool bit 31, a recess 30', and a torque limiting and locking spring 20'. The elongated tool bit 31 is adapted to engage with interchangeable bone screws. The elongated tool bit 31 can either be composed of a single piece that extends into the handle as shown in FIG. 11, or optionally composed of two separated pieces, a driver shaft 16 and a tool bit 14, as shown in FIGS. 1-3. Multiple elongated tool bits are provided, each having different tips to engage with different configurations of bone screws.

A recess 30' is disposed along the handle 12' such that the inside of the handle is externally visible. An elongated opening 22' extends through the handle 12'. The elongated tool bit 31 is adapted to be received in the opening 22'. The elongated tool bit 31 is inserted into the opening 22' and comes to rest at the thrust bearing surface 26' inside the handle 12' as shown in FIG. 11.

A slot 28', which includes a flat surface 29' (as shown in FIG. 11), is provided in each of the elongated tool bits 31 and is brought into alignment with the recess 30' formed the handle 12'. The slot 28' formed by the flat surface 29' is axially positioned on the elongated tool bit so that when the elongated tool bit 31 is inserted up, into and in abutment to the thrust bearing surface 26', slot 28' of the elongated tool bit 31 is brought into alignment with the recess 30' in the handle 12'. Thus, a spring 20' can be inserted to secure the elongated tool bit 31 within the handle 12'.

When the slot 28' of the elongated tool bit 31 is brought into alignment with the recess 30', the spring 20' is inserted into the recess 30' to secure the elongated tool bit 31 into the handle 12' and thereby prevent any actual displacement of the elongated tool bit. Removal of the spring to permit replacement of the elongated tool bit is provided by snapping the spring 20' on or off thereby permitting the elongated tool bit to be easily removed and/or attached. It should be noted that the torque limiting spring 20 can be used as an alternative to the spring 20' in this embodiment of the instant invention, without departing from the scope of the invention.

Figure 8:
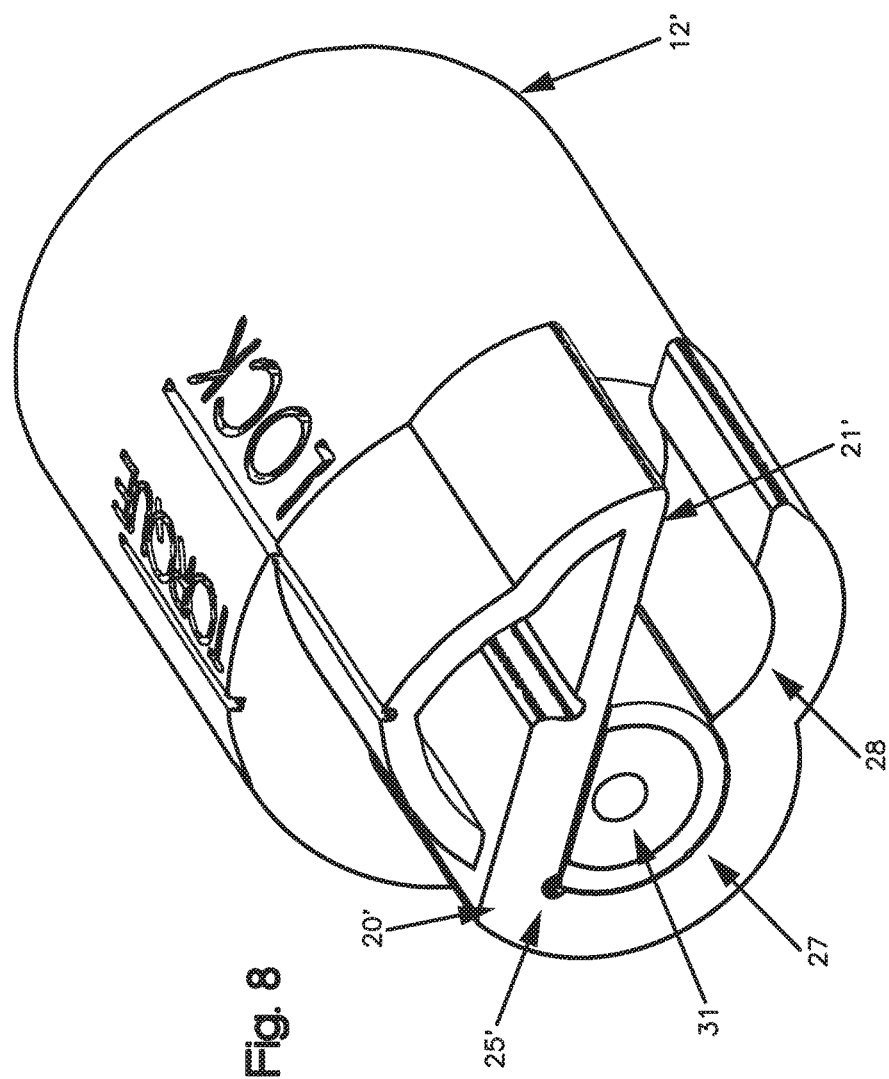
FIG. 8 is an exploded view of the driver shaft, tool bit and torque limiting spring in the "lock position" constructed in accordance an embodiment of the instant invention.

Additionally, in this position, the spring 20' will rest against the flat surface 29' during each rotation of the handle 12'. The spring 20' comprises at least a first arm having first and second opening (27 and 28) and a flat arm 21'. The spring 20' also comprises a notch 25' where the first arm and the flat arm meet. A first opening 27 of the spring 20' is designed such that it will not disengage from the elongated tool bit 31, regardless of the amount of torque applied to the screwdriver. That is, the user can impart unrestricted torque to the universal screwdriver in the "lock" position of the spring 20' without spring 20' being displaced when used in the position as shown in FIG. 8.

Figure 9:
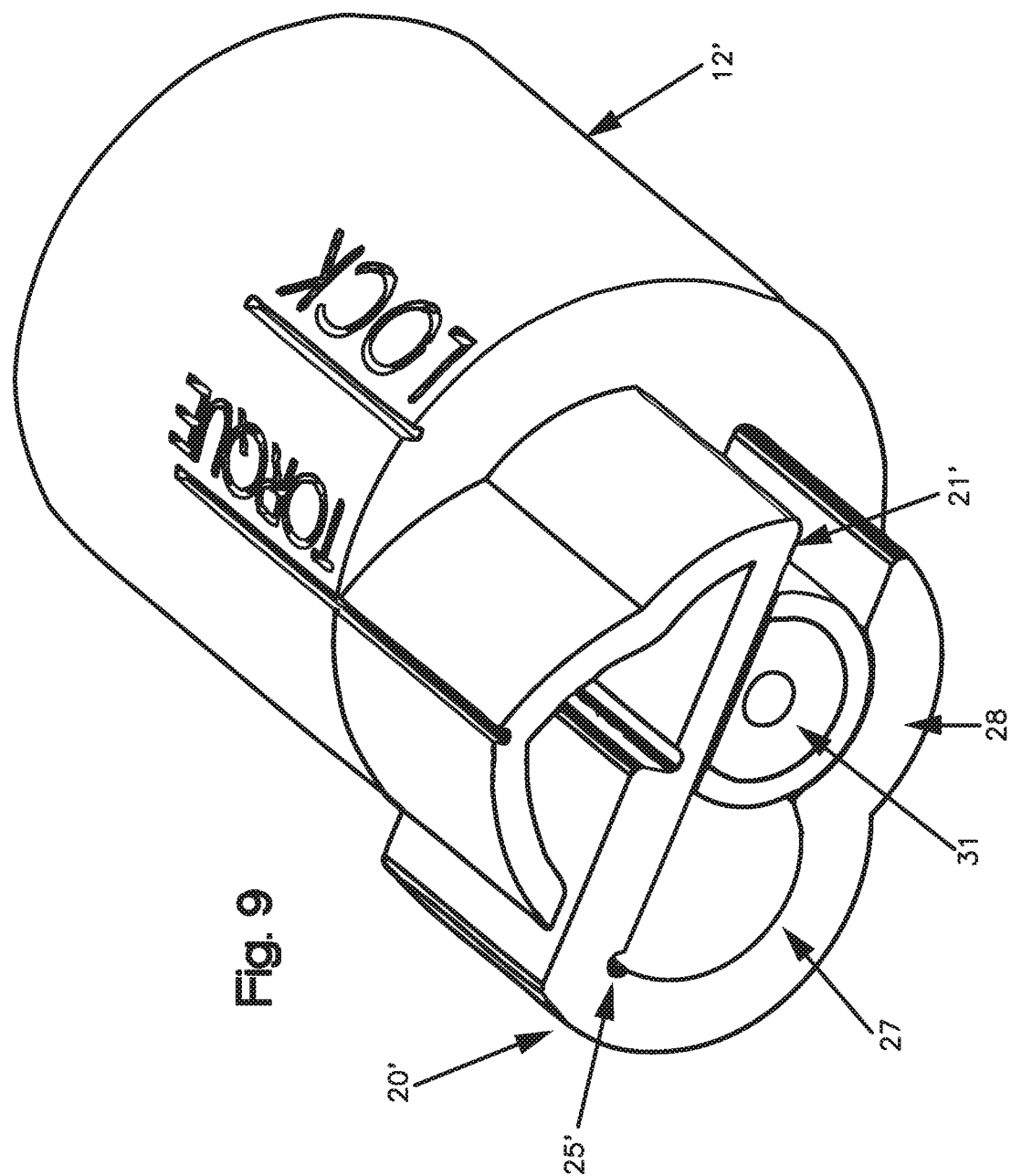
FIG. 9 is an exploded view of the driver shaft, tool bit and torque limiting spring in the "torque position" constructed in accordance an embodiment of the instant invention.

The second opening 28 is designed such that the spring 20' will disengage from the elongated tool bit 31 after a sufficient amount of torque is applied to the screwdriver 10' in use. When the universal screwdriver 10' is assembled and the spring 20' is positioned such that the second opening 28 engages the elongated tool bit 31 as shown in FIG. 9, as the user applies torque to the screwdriver, the elongated tool bit 31 will encounter resistance. When such resistance exceeds the pre-set torque value of the torque limited spring 20', the spring 20' will become disengaged, and accordingly the screwdriver 10' will no longer be able to impart force on the elongated tool bit 31. Accordingly, the handle 12' can continue to be rotated, but the elongated tool bit 31 will have ceased rotating, thus inhibiting a user from over-tightening a screw into the bone or bone plate. The user can select the desired torque limitation by utilizing a spring 20' that conforms to the user's needs.

In another embodiment, as shown in FIG. 11, the elongated tool bit 31 may be hollow along the longitudinal axis in order to accept a Kershner wire, or the like, along such longitudinal axis and create a continuous channel with a cannulated screw.

It should be noted that the spring 20 or 20' could be located at any position along the elongated tool bit 31 depicted in FIGS. 9-11 without departing from the scope of invention.

Thus, while there have been shown and described and pointed out novel features of the present invention as applied to preferred embodiments thereof, it will be understood that various omissions and substitutions and changes in the form and details of the disclosed invention may be made by those skilled in the art without departing from the spirit of the invention. It is the intention, therefore, to be limited only as indicated by the scope of the claims appended hereto.

It is also to be understood that the following claims are intended to cover all of the generic and specific features of the invention herein described and all statements of the scope of the invention which, as a matter of language, might be said to fall there between. In particular, this invention should not be construed as being limited to the dimensions, proportions or arrangements disclosed herein.

What is claimed is:

1. An orthopedic universal screwdriver comprising:
   a handle having a slot that is adapted to receive an elongated tool bit, wherein the elongated tool bit has a hollow center along a longitudinal axis;
   a recess disposed in said handle; and
   a torque limiting and locking spring comprising at least two arms, wherein the first arm is a flat arm and the second arm has at least two openings, wherein the torque limiting and locking spring is removeably attachable to the handle via said recess for securing the elongated tool bit in at least one of the openings to said handle.

2. The orthopedic universal screwdriver of claim 1, wherein the torque limiting and locking spring is capable of preventing over tightening of a bone screw.

3. The orthopedic universal screwdriver of claim 1, wherein the first arm comprises a first interior surface and the second arm comprises a second interior surface, and said torque limiting and locking spring further comprises a notch at a position where the first and second interior surfaces are joined together.

4. The orthopedic universal screwdriver of claim 1 wherein
   a flat surface on the elongated tool bit and configured to align with the recess when said elongated tool bit is inserted into said handle and
   said torque limiting and locking spring being constructed to and positioned to engage the flat surface on the elongated tool bit.

\* \* \* \* \*